United States Patent [19]

Frommeld et al.

[11] 3,944,423

[45] Mar. 16, 1976

[54] LIGHT-SENSITIVE DIAZOTYPE MATERIAL COMPRISING A FLUOROALKOXY-SUBSTITUTED DIAZONIUM COMPOUND

[75] Inventors: Hans-Dieter Frommeld; Herbert Rauhut, both of Wiesbaden-Biebrich, Germany

[73] Assignee: Keuffel & Esser Company, Morristown, N.J.

[22] Filed: Sept. 2, 1969

[21] Appl. No.: 854,720

[30] Foreign Application Priority Data

Sept. 3, 1968 Germany ........................... 1793331

[52] U.S. Cl. ..................... 96/91 R; 96/27 R; 96/33; 260/141; 260/142

[51] Int. Cl.$^2$ .................... G03C 1/54; C07C 113/00

[58] Field of Search ................. 260/141, 142; 96/91

[56] References Cited

UNITED STATES PATENTS

| | | | |
|---|---|---|---|
| 3,081,166 | 3/1963 | Van Loon et al. | 260/141 X |
| 3,281,245 | 10/1966 | Werner et al. | 260/141 X |
| 3,290,150 | 12/1966 | Eenshuistra et al. | 260/141 X |
| 3,379,531 | 4/1968 | Mizianty et al. | 260/141 X |
| 3,442,650 | 5/1969 | Hendrickx et al. | 260/141 X |
| 3,539,347 | 11/1970 | Rauhut | 260/141 X |

*Primary Examiner*—Floyd D. Higel
*Attorney, Agent, or Firm*—Lionel N. White

[57] ABSTRACT

Diazotype material includes a light-sensitive diazonium compound of the general formula

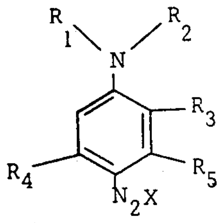

wherein:

$R_1$ and $R_2$ are substituted or unsubstituted alkyl, aralkyl, or cycloalkyl groups, or form, with the nitrogen atom, a heterocyclic radical, which may be substituted;

$R_3$ is hydrogen or the group $OR_6$;

$R_4$ and $R_5$ are hydrogen, halogen, alkyl, or $OR_6$ groups;

$R_6$ is alkyl; or fluorinated alkyl, alkenyl, cycloalkyl, or cycloalkenyl; and

X is the anion of the diazonium compound;

at least one of the radicals $R_4$ and $R_5$ is hydrogen; and at least one of the radicals $R_3$, $R_4$, and $R_5$ is one of said fluorinated radicals, at least one of said fluorinated radicals being further substituted by other halogen atoms, hydroxy groups, acyloxy groups, alkoxy groups, alkylated or acylated amino groups, or aryl radicals.

5 Claims, No Drawings

LIGHT-SENSITIVE DIAZOTYPE MATERIAL COMPRISING A FLUOROALKOXY-SUBSTITUTED DIAZONIUM COMPOUND

BACKGROUND OF THE INVENTION

It is known to use, as the light-sensitive substance in photoprinting materials, benzene diazonium compounds carrying in 4-position to the diazo group a tertiary amino group which is substituted by alkyl or aralkyl groups, or whose nitrogen atom is a component of a heterocyclic radical.

These compounds may contain further substituents in the benzene ring, e.g. alkyl or alkoxy groups, preferably in 2- or 5-position to the diazo group.

The properties which render these compounds suitable for diazotype purposes are largely determined by these substituents.

Thus, the light-sensitivity of the compound is considerably increased by the presence of an alkoxy group in 5-position to the diazo group, while the same group, when in 2-position, decreases the light-sensitivity of the compound.

A combination of one alkoxy group each in the 2- and in the 5-position of the benzene ring, which results in highly light-sensitive and at the same time stable diazonium compounds, has proved especially suitable for practical purposes. The light-sensitivity may also be influenced by the type of the tertiary amino group in the 4-position. It is increased, for example, by the presence of a pyrrolidino radical in this position. The radicals attached to the nitrogen atom affect mainly the coupling speed of the diazo compounds. Lower alkyl groups cause a lower coupling speed than do those with longer carbon chains or aralkyl groups. Heterocyclic radicals instead of a tertiary amino group with aliphatic radicals also normally cause an increase in the coupling speed, but there are wide differences in this respect, e.g., between the readily coupling morpholino compounds and the relatively slow-coupling pyrrolidino compounds. As a further possibility of increasing the coupling speed, the carbon chains of the alkoxy groups in the benzene nucleus may be extended. The readily coupling compounds are used mainly for one-component materials, while the less rapidly coupling compounds are used for two-component materials.

Recently, it has been found that the coupling speed, particularly of highly light-sensitive photoprinting materials, is not sufficient for certain purposes. Thus, for processing two-component materials, photoprinting apparatus is available which is equipped with a powerful light-source which renders it possible to use relatively short exposure times. When development, e.g. ammonia development, is to be effected in the same apparatus, the working speed utilized in exposure cannot be maintained in the development step, because in this case the disproportionately low coupling speed requires a longer resident time of the material. Nor is it possible to balance this drawback simply by using a more active coupling component, because this would mean an undue restriction of the choice of color shades available. This drawback is particularly evident in the case of materials with transparent supports, e.g. plastics films or lacquered transparent papers, because the necessary quantities of water vapor and ammonia penetrate less easily into the surface of these materials than into that of normal photoprinting papers.

Also in the case of one-component diazotype materials, there is a tendency to use diazo compounds of greater coupling speed. Here it is, above all, the desire to replace the alkaline developer solutions normally used hitherto by solutions having a neutral or weakly acid reaction, because such solutions are considerably more stable than alkaline solutions. However, the coupling reaction proceeds considerably more slowly at lower pH values, so that the choice of highly active diazo compounds available for this purpose is very limited.

It is known from Belgian Pat. No. 676,820 that diazonium compounds having a trifluoromethyl group in 3-position to the diazo group exhibit a higher coupling speed than do unsubstituted compounds.

It has also been suggested in U.S. Pat. No. 3,539,347 to use diazonium compounds derived from unilaterally diazotized p-phenylene diamine and containing fluorinated alkoxy radicals in o-position and/or in m-position to the diazonium group, which radicals contain no further substituents besides fluorine and hydrogen atoms.

SUMMARY OF THE INVENTION

It is an object of the present invention to provide diazo compounds which possess a higher coupling speed than the compounds hitherto known, in combination with an about equal light-sensitivity.

According to the present invention, a diazonium compound derived from unilaterally diazotized p-phenylene diamine is provided which corresponds to the following general formula

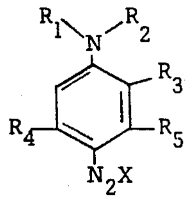

wherein:

$R_1$ and $R_2$ are substituted or unsubstituted alkyl, aralkyl, or cycloalkyl groups, or form, with the nitrogen atom, a heterocyclic radical which may be substituted;

$R_3$ is hydrogen or the group $OR_6$;

$R_4$ and $R_5$ are hydrogen, halogen, alkyl or $OR_6$ groups;

$R_6$ is alkyl; or fluorinated alkyl, alkenyl, cycloalkyl or cycloalkenyl; and

X is the anion of the diazonium compound;

at least one of the radicals $R_4$ and $R_5$ is hydrogen; and at least one of the radicals $R_3$, $R_4$ and $R_5$ is one of said fluorinated radicals, at least one of said fluorinated radicals being further substituted by other halogen atoms, hydroxy groups, acyloxy groups, alkoxy groups, alkylated or acylated amino groups, or aryl radicals.

Because of their easier availability, such compounds are preferred in which the fluorinated radical or radicals contain halogen atoms or aryl radicals as further substituents.

Further, the present invention provides a diazotype material carrying a light-sensitive one-component or two-component layer, which is characterized in that it contains one of the above-described novel diazonium compounds as the light-sensitive substance.

The diazonium compounds used in accordance with the present invention are distinguished by a coupling speed which is considerably higher than that of compounds containing unsubstituted alkoxy groups instead of the fluorinated ether groups. The coupling speed of the diazonium compounds increases about equally when either one of the groups $R_3$ or $R_4$ or $R_5$ is a fluorinated ether group. Compounds containing two fluorinated ether groups possess an even higher coupling activity. Surprisingly, the light-sensitivity of the compounds is increased when the fluorinated ether group is in o-position to the diazo group.

Normally the fluorinated radicals have not more than 5 carbon atoms in the aliphatic chain and not more than 6 carbon atoms in the cycloaliphatic ring, because the compounds become too difficultly soluble or too surface-active with longer carbon fluoride chains or fluorinated rings with too many members. Fluorinated arylalkoxy groups may contain up to 10 carbon atoms.

The following radicals (in which D stands for the appropriate benzene diazonium residue) are examples of suitable substituted alkoxy groups containing fluorine:

$D—O—CFCl_2$
$D—O—CF_2Cl$
$D—O—CF_2—CH_2Cl$
$D—O—CF_2—CHFCl$
$D—O—CF_2—CHFBr$
$D—O—CF_2—CHFI$
$D—O—CF_2—CHF—CH_2—CH_2—Br$
$D—O—CF_2—CHF—CH_2—CH_2—N(CH_3)_2$
$D—O—CF_2—CBr_2H$
$D—O—CF_2—C_6H_5$
$D—O—CF_2—CHF—C_6H_4Cl$
$D—O—CH(CF_3)—CCl_3$
$D—O—CH(CF_2Cl)_2$
$D—O—CH_2—(CF_2)_3—CH_2—OH$

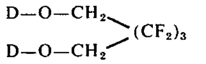

$D-O-CH_2-(CF_2)_3-CH_2-O-CH_3$

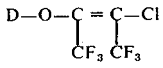

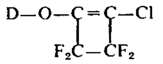

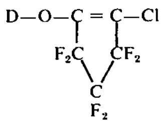

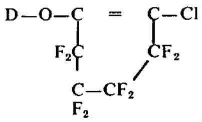

All other substituents attached to the nucleus and to the amino nitrogen are known in the diazotype art and their effect has already been described. Normally, the alkyl radicals in the tertiary amino group contain not more than 5 carbon atoms and may be further substituted in known manner, e.g. by halogen, or hydroxy or amino groups, and have straight or branched chains. Cycloalkyl groups and aralkyl groups in this position normally contain not more than 10 carbon atoms, substituted or unsubstituted benzyl groups and substituted or unsubstituted cyclohexyl groups being preferred. When $R_1$ and $R_2$ form a heterocyclic radical with the tertiary nitrogen atom, this radical may be derived in known manner from pyrrolidine, piperidine, piperazine, N-methyl-piperazine, thiomorpholine, morpholine, 2-methyl-morpholine,2,6-dimethyl-morpholine, hexamethyleneimine, and others.

When the radicals $R_4$ and $R_5$ are alkyl groups, they do not normally contain more than 2 carbon atoms, methyl groups being preferred. The substituents attached to the benzene nucleus may be the alkoxy radicals frequently used in diazotype materials. These radicals, which in turn may be further substituted, e.g. by hydroxyl groups, contain preferably up to 5 carbon atoms in a straight or branched chain. Examples of such groups are methoxy, ethoxy, isopropoxy, n-butoxy, isobutoxy, hydroxyethoxy, ethoxy-ethoxy groups and the like.

The diazonium compounds according to the invention may be used for one-component or for two-component diazotype materials, depending on the kind of substituents selected.

The novel diazonium compounds according to the present invention are separated in the conventional manner in the form of their stable double salts or complex salts. They are of good compatibility with the conventional stabilizers and additives, such as citric acid, sulfosalicilic acid, thiourea, naphthalene-1,3,6-trisulfonic acid, zinc chloride etc.

As is usual, paper, transparent paper, transparentized paper, and plastic films suitable for sensitization with diazo compositions, may be used as supports.

The novel compounds may be prepared in analogy to known processes by one of the following methods:

A. 2-Chloro-4-ethoxy-phenol is etherified with 1,1-difluoro-1,2,2-trichloroethane in dimethyl formamide in the presence of potassium hydroxide to yield the 2-chloro-1-(1′,1′-difluoro-2′,2′-dichloro-ethoxy)-4-ethoxy-benzene. This compound is then nitrated in the 5-position, and the chlorine atom in the 2-position is replaced by an aliphatic amine, preferably a heterocyclic base, such as morpholine, pyrrolidine, piperazine, thiomorpholine, or substitution products thereof. The desired diazo compound is then obtained by reduction and diazotization in the normal manner.

B. A hydroquinone monoalkyl ether is etherified with trifluorochloroethylene in acetone, in the presence of potassium hydroxide, to yield the 4-(1′,1′,2′-trifluoro-2′-chloro-ethoxy)-1-alkoxy-benzene. This may then be nitrated in the 2-position, reduced, and alkylated to form the tertiary base. The compound is then again nitrated, reduced, and diazotized in the normal manner.

C. 3-Dialkylamino-phenol is etherified with trifluorochloroethylene in an acetone/potassium hydroxide mixture. By coupling with diazotized p-nitroaniline, followed by reduction, an amino group is introduced in the 6-position, which may then be converted in the normal manner into a diazo group.

D. The benzyl group of 4-nitro-3-chloro-6-benzyloxy-N,N-dialkylaniline — which compound can be easily prepared analogously to known compounds — is split off by heating with hydrochloric acid. The phenol thus produced is then etherified by radicals containing fluorine, e.g. with 1,2-dichloro-hexafluoro-cyclopenten-(1) in the presence of potassium hydroxide. The nitro compound is converted into the diazonium compound in the normal manner.

The methods of preparation stated above are only meant as examples. Other methods may also be used for the preparation of fluorinated alkylaryl ethers carrying further substituents in the alkyl residue. The substitution of activated nuclear halogen by fluorinated alcohols, e.g. trichloro-trifluoropropanol-(2), or the subsequent introduction of fluorine into the aliphatic alkyl group of the ether by substitution are only mentioned as examples.

The starting materials for the preparation of the fluorinated ethers described are commercially available.

PREFERRED EMBODIMENTS

Example 1

White photoprinting base paper provided with a precoat of finely divided silica and polyvinyl acetate, was coated with a solution of the following composition and dried:

4.0 g. of citric acid
5.0 g. of thiourea
1.4 g. of 2-hydroxy-3-naphthoic acid-(β-morpholinoethyl)-amide
1.6 g. of 4-diethylamino-2-(1′,1′,2′-trifluoro-2′-chloroethoxy)-benzene diazonium chloride, in the form of the zinc chloride double salt, in
100 ml. of water After exposure under an original and development with ammonia, images with strong blue lines were obtained. With the use of this material, the full color areas of the blue image were produced within a shorter time than when using 4-diethylamino-2-ethoxy-benzene diazonium chloride (zinc chloride double salt) in an otherwise identical coating composition.

Example 2

Transparent paper lacquered with cellulose acetate was coated with a solution of the following composition and dried:

65.0 ml. of isopropanol
25.0 ml. of water
3.5 g. of citric acid
3.5 g. of thiourea
2.2 g. of 4-morpholinomethyl-2,5-dimethylphenol, hydrochloride,
3.2 g. of 4-morpholino-2-ethoxy-5-(1′,1′-difluoro-2′,2′-dichloro-ethoxy)-benzene diazonium chloride, in the form of the zinc chloride double salt, and
5.0 g. of formic acid After imagewise exposure of the sensitized material under an original and development with gaseous ammonia, yellow images of very good covering power were obtained, while the image-free areas were of good transparency.

As compared with a material prepared according to the same recipe but with the known 4-morpholino-2,5-diethoxy-benzene diazonium chloride as the zinc chloride double salt, the final point of the coupling was reached distinctly earlier with the material according to the invention. The covering capacity of the copies produced according to the invention also was markedly better.

Example 3

Cellulose acetate film was coated with a solution of the following composition and dried:

15.0 ml. of water
22.5 ml. of isopropanol
4.0 g. of thiourea
1.5 g. of sulfosalicylic acid
1.0 g. of 3-hydroxy-4-methyl-phenyl urea
2.2 ml. of formic acid (85%), and
2.7 g. of 4-morpholino-5-methoxy-2-(1′,1′,2′-trifluoro-2′-chloro-ethoxy)-benzene diazonium tetrafluoborate.

After imagewise exposure of the sensitized material under an original and development with gaseous ammonia, yellow images of excellent covering power within the near ultraviolet light range were obtained, whereas the image-free areas showed a good transparency.

When 2.5 g. of the zinc chloride double salt of 4-morpholino-2,5-diethoxy-benzene diazonium chloride were used instead of the above mentioned diazonium compound in an analogous experiment, the comparison test showed that the material according to the invention couples more rapidly during development, has a better covering power, and is also more light-sensitive.

When blue coupling components are included in the formulation, black lines are produced. Cellulose ester-coated polyester films, polycarbonate films, and other suitable plastic films may also be used as supports.

Example 4

A photoprinting base paper customarily used for diazotype purposes, which was provided on one side with a precoat of finely divided silica and polyvinyl acetate, was coated, on the precoated surface, with an aqueous solution containing, per 100 ml of solution:

0.6 g. of tartaric acid,
0.02 g. of saponin, and
1.5 g. of 4-diethylamino-5-ethoxy-2-(1′,1′,2′-trifluoro-2′-chloroethoxy)-benzene diazonium chloride, as the zinc chloride double salt, and then dried.

The sensitized photoprinting material was imagewise exposed under a transparent original and developed by means of an aqueous solution containing, per 100 ml of solution:

2.5 g. of borax
3.0 g. of soda
2.0 g. of common salt
5.0 g. of thiourea
0.1 g. of the sodium salt of isopropylnaphthalene sulfonic acid
0.6 g. of resorcinol, and
0.6 g. of phloroglucinol Brownish-black copies were obtained which were very rich in contrast.

The full coupling color shade was produced immediately after application of the developer solution. The above-mentioned diazo compound could be replaced, with equally good results, by 2.0 g of 4-pyrrolidino-3-[2′-chloro-3′,3′,4′,4′,5′,5′-hexafluoro-cyclopentene-(1′)-yloxy]-benzene diazonium chloride, in the form of the zinc chloride double salt.

EXAMPLE 5

A photoprinting base paper of the kind customarily used for diazo-type purposes was coated with an aqueous solution containing, per 100 ml of solution:

0.5 g. of citric acid
0.5 g. of gum arabic
3.5 g. of the sodium salt of naphthalene-1,3,6-trisulfonic acid, and
1.8 g. of 4-(N-methyl-N-benzyl-amino)-2-chloro-5-(1′,1′,2′-trifluoro-2′-chloro-ethoxy)-benzene diazonium tetrafluoborate and then dried.

The sensitized photoprinting material was imagewise exposed under a transparent original and developed with an aqueous solution which contained, per 100 ml of solution:

0.33 g. of phloroglucinol
9.60 g. of trisodium citrate
2.42 g. of sodium benzoate
1.97 g. of adipic acid
5.70 g. of common salt, and
0.20 g. of the sodium salt of a dialkyl naphthalene sulfonic acid and had a pH value of about 6.

Upon the application of the developer, black images very rapidly appeared on a white background.

In the following Table, by reference to specific substituents, further compounds are listed which were prepared and tested as in the foregoing Examples with equally good results.

TABLE

| Melting pt. of Nitro Comp. (°C.) | | $R_1$ - N - $R_2$ | $R_3$ | $R_4$ | $R_5$ | X |
|---|---|---|---|---|---|---|
| 1. | 102° | 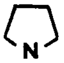 | $—O—CF_2—C_6H_5$ | H | H | $Cl^-$ $.ZnCl_2/2$ |
| 2. | 111° | 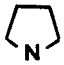 | 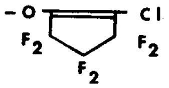 | H | H | $Cl^-$ $.ZnCl_2/2$ |
| 3. | 63° | 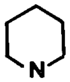 | 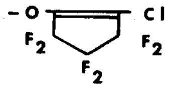 | H | H | $Cl^-$ $.ZnCl_2/2$ |
| 4. | 155° | 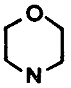 | 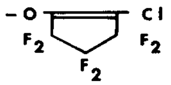 | H | H | $Cl^-$ $.ZnCl_2/2$ |
| 5. | 116° | 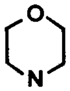 | 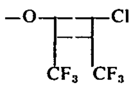 | H | H | $Cl^-$ $.ZnCl_2/2$ |
| 6. | 88° | 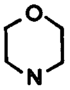 | $—O—CF_2—CHFCl$ | H | H | $BF_4^-$ |
| 7. | 114° | $CH_3—N—CH_3$ | 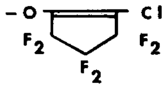 | Cl | H | $Cl^-$ $.ZnCl_2/2$ |
| 8. | Oil | $CH_3—N—CH_2$- 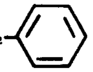 | $—O—CF_2—CHFCl$ | Cl | H | $BF_4^-$ |
| 9. | 120° | 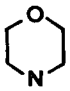 | $—O—CF_2—CCl_2H$ | $—O—C_2H_5$ | H | $Cl^-$ $.ZnCl_2/2$ |
| 10. | 102° | $C_2H_5—N—C_2H_5$ | $—O—C_2H_5$ | $—O—CF_2—CHFCl$ | H | $Cl^-$ $.ZnCl_2/2$ |
| 11. | 72° | $CH_3—N—CH_2$- 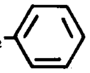 | $—O—CH_3$ | $—O—CF_2—CHFCl$ | H | $BF_4^-$ |
| 12. | 78° | $HO—CH_2—CH_2—N\ CH_2$- 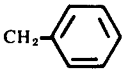 | $—O—CH_3$ | $—O—CF_2—CHFCl$ | H | $BF_4^-$ |
| 13. | Oil | $O—CO—CH_3$ \| $CH_2—CH_2—N—CH_2$- 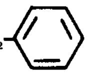 | $—O—CH_3$ | $—O—CF_2—CHFCl$ | H | $Cl^-$ $.SnCl_4$ |
| 14. | 116° | 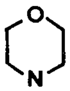 | $—O—CH_3$ | $—O—CF_2—CHFCl$ | H | $BF_4^-$ |
| 15. | 82° | 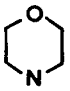 | $—O—C_4H_9$ | $—O—CF_2—CHFCl$ | H | $BF_4^-$ |
| 16. | 81° | 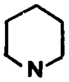 | $—O—CH_3$ | $—O—CF_2—CHFCl$ | H | $Cl^-$ $.ZnCl_2/2$ |
| 17. | 57° | 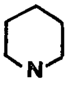 | $—O—C_4H_9$ | —O—CF- | H | $Cl^-$ $.ZnCl_2/2$ |

TABLE-continued

| | Melting pt. of Nitro Comp. (°C.) | $R_1$ - N - $R_2$ | $R_3$ | $R_4$ | $R_5$ | X |
|---|---|---|---|---|---|---|
| | | | | $_2$—CHFCl | | |
| 18. | 78° | 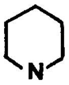 | —O—$CH_2$—CH-$_2$—O—$C_2H_5$ | —O—CF-$_2$—CHFCl | H | $Cl^-$ .$ZnCl_2$/2 |
| 19. | Oil (Amine 77°) | 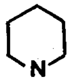 | —O—$CH_2$—CH-$_2$—N($C_2H_5$)$_2$ | —O—CF-$_2$—CHFCl | H | $Cl^-$ .$SnCl_4$ |
| 20. | Dyestuff with diazotized p-Nitroaniline 153° | $C_2H_5$—N—$C_2H_5$ | H | —O—CF-$_2$—CHFCl | H | $Cl^-$ .$ZnCl_2$/2 |
| 21. | Oil | $CH_3$—N—$CH_3$ | —O—$CH_2$—CH-$_2$—O—$CH_3$ | H | —O—CF-$_2$—CHFCl | $Cl^-$ .$ZnCl_2$/2 |
| 22. | 80° | 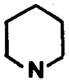 | $OCH_3$ | —O—CF-$_2$—CHFBr | H | $Cl^-$ .$ZnCl_2$12 |

The above examples have been presented for the purpose of illustration and should not be taken to limit the scope of the present invention. It will be apparent that the described examples are capable of many variations and modifications which are likewise to be included within the scope of the present invention as set forth in the appended claims.

What is claimed is:

1. Diazotype material comprising a support having coated thereon a light-sensitive composition comprising a diazonium compound wherein said diazonium compound is 4-diethylamino-2-(1′,1′,2′-trifluoro-2′-chloro-ethoxy)-benzene diazonium chloride.

2. Diazotype material comprising a support having coated thereon a light-sensitive composition comprising a diazonium compound wherein said diazonium compound is 4-morpholino-2-ethoxy-5-(1′,1′-difluoro-2′,2′-dichloro-ethoxy)-benzene diazonium chloride.

3. Diazotype material comprising a support having coated thereon a light-sensitive composition comprising a diazonium compound wherein said diazonium compound is 4-morpholin methoxy-2-(1′,1′,2′-trifluoro-2′-chloro-ethoxy)-benzene diazonium tetrafluoborate.

4. Diazotype material comprising a support having coated thereon a light-sensitive composition comprising a diazonium compound wherein said diazonium compound is 4-diethylamino-5-ethoxy-2-(1′,1′,2′-trifluoro-2′-chloro-ethoxy)-benzene diazonium chloride.

5. Diazotype material comprising a support having coated thereon a light-sensitive composition comprising a diazonium compound wherein said diazonium compound is 4-pyrrolidino-3-[2′-chloro-3′,3′,4′,4′,5′,-5′-hexafluoro-cyclopentene-(1′)-yloxy]-benzene diazonium chloride.

* * * * *